United States Patent [19]

Merger et al.

[11] Patent Number: 5,256,813
[45] Date of Patent: Oct. 26, 1993

[54] 3-SUBSTITUTED 2-HYDROXY-3-FORMYLPROPIONIC ESTERS, THE PREPARATION THEREOF AND THE USE THEREOF FOR PREPARING 3-SUBSTITUTED 3-FORMYLACRYLIC ESTERS

[75] Inventors: Franz Merger, Frankenthal; Juergen Frank, Limburgerhof, both of Fed. Rep. of Germany

[73] Assignee: BASF Aktiengesellschaft, Ludwigshafen, Fed. Rep. of Germany

[21] Appl. No.: 883,342

[22] Filed: May 15, 1992

Related U.S. Application Data

[62] Division of Ser. No. 593,891, Oct. 5, 1990, Pat. No. 5,202,461.

[30] Foreign Application Priority Data

Oct. 6, 1989 [DE] Fed. Rep. of Germany ....... 3933334

[51] Int. Cl.$^5$ .................. C07C 69/675; C07C 69/732
[52] U.S. Cl. ...................................... 560/177; 560/212
[58] Field of Search ................................ 560/177, 212

[56] References Cited

U.S. PATENT DOCUMENTS

| | | | |
|---|---|---|---|
| 3,984,440 | 10/1976 | Bollag et al. | 568/424 |
| 4,215,215 | 7/1980 | Bollag et al. | 548/518 |
| 4,230,872 | 10/1980 | Klaus et al. | 548/527 |
| 4,656,310 | 4/1987 | Bollag et al. | 568/9 |

*Primary Examiner*—José G. Dees
*Assistant Examiner*—B. Frazier
*Attorney, Agent, or Firm*—Oblon, Spivak, McClelland, Maier & Neustadt

[57] ABSTRACT

A 3-substituted 2-hydroxy-3-formylpropionic ester of the formula I

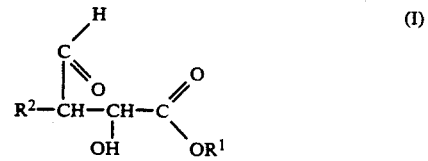

where
R$^1$ is lower alkyl, and R$^2$ is straight-chain or branched alkyl of 1 to 10 carbon atoms, is obtained by adding an alkanal of the fomrula II

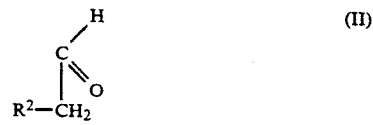

and an alkyl glyoxylate of the formula III

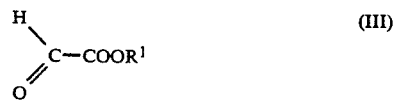

simultaneously to a catalyst system composed of a salt or a mixture of a secondary amine and a carboxylic acid in such a way that the temperature does not exceed 90° C., preferably 80° C., or else adding one of the reactants of the formula II or III to a mixture of the catalyst system described above and the other reactant in such a way that the temperature does not exceed 90° C. The 2-hydroxy-3-formylpropionic eater of the formula I can be converted by treatment with dehydrating agents, especially acetic anhydride, into good yields of the corresponding 3-substituted 3-formylacrylic ester.

5 Claims, No Drawings

3-SUBSTITUTED 2-HYDROXY-3-FORMYLPROPIONIC ESTERS, THE PREPARATION THEREOF AND THE USE THEREOF FOR PREPARING 3-SUBSTITUTED 3-FORMYLACRYLIC ESTERS

This is a division of application Ser. No. 07/593,891, filed on Oct. 5, 1990, now U.S. Pat. No. 5,202,461.

The present invention relates to 3-substituted 2-hydroxy-3-formylpropionic esters of the formula I

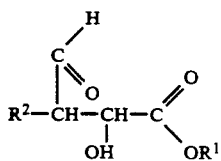

where
$R^1$ is alkyl of 1 to 4 carbon atoms, and $R^2$ is straight-chain or branched alkyl of 1 to 10 carbon atoms, a process for the preparation thereof and the use thereof for preparing 3-substituted 3-formylacrylic esters.

3-Substituted 3-formylacrylic esters are precursors required for preparing compounds with pharmacological activity.

For example, in the simplest case where the substituent in the 3-position is methyl the compound is a 3-formylcrotonic ester which is required for preparing vitamin A acid.

Besides a number of laboratory methods which, via oxidation of one of the two methyl groups in esters of senecioic acid (3,3-dimethylacrylic acid), yield esters of formylcrotonic acid (cf. J. Am. Chem. Soc. 82, (1960) 2286-88; Tetrahedron Letters 1976, 3985-86; Synthesis 1983, 297-300), processes which can be used for the industrial production of the desired compounds have also been disclosed.

However, even the best processes are still associated with serious disadvantages. For example, Wittig-Horner reactions between acetals of methylglyoxal and phosphonoacetic esters have the disadvantage that the starting materials have to be prepared in multistage syntheses which entail the use of toxic or aggressive substances. Thus, for example, methylglyoxal dimethyl acetal is prepared by nitrosation of acetone (cf. Pure Appl. Chem. 43, (1975) 450). To prepare the second required component, the phosphonoacetic ester, it is necessary to react a trialkyl phosphite with a highly lacrimatory bromoacetic ester. The alkyl bromides which are formed as by-products are increasingly under suspicion of being carcinogenic. Overall, the Wittig-Horner synthesis is, owing to these complications, difficult to control, complicated and thus uneconomic.

Procedures for Wittig-Horner reactions are disclosed in the literature (cf., for example, J. Chem. Soc., Perkin Trans. I, 1987, 1743-48).

It has also been disclosed in DE 1 008 729 that alpha-hydroxy-alpha-alkoxyacetic esters can undergo with propionaldehyde a condensation which is catalyzed by dialkylamines to give 3-formylcrotonic esters. In this process, the reaction components are initially introduced and then the catalyst is added to start the exothermic reaction.

This procedure cannot be carried out on the industrial scale for safety reasons (see Comparative Examples 1 to 3). Moreover, the yields which can be achieved are not entirely satisfactory.

A recent article in J. Org. Chem. 52 (1987), 4788-90, describes in detail the serious problems experienced by various groups when they attempted to react glyoxylic acid with carbonyl compounds. Particular difficulties were experienced when attempting to react aliphatic aldehydes with glyoxylic acid (cf. loc. cit. 4788). For example, the reaction of aliphatic aldehydes with glyoxylic acid in the presence of morpholine produced essentially only butenolides. As a way out of this dilemma, it is stated in the loc. cit. that 3-formyl-3-alkylacrylic esters can be obtained quite satisfactorily when enamines of the aldehydes are reacted with glyoxylic esters or the hemiacetals thereof and then the resulting adducts are hydrolyzed. The disadvantage of this process is that the free alkanals, which are readily available, cannot be employed, and it is necessary to use the enamines thereof. However, the enamines of lower alkanals, in particular, are not easy to obtain industrially. Furthermore, the hydrolysis must be carried out under tightly controlled conditions (see loc. cit. 4789, right-hand column, lines 18-20). In addition, the amine used as auxiliary reagent must be employed in stoichiometric amount and, after the hydrolysis, is in the form of a solution in a mineral acid. It can be recovered from the latter only in an elaborate way by neutralization and extraction or distillation.

It is an object of the present invention to develop a more reasonable process for preparing 3-substituted 3-formylacrylic esters from glyoxylic esters and alkanals, starting from free alkanals and avoiding the disadvantages of the prior art.

We have found that this object is achieved by reacting glyoxylic esters with free alkanals in the presence of mixtures or salts of secondary amines and carboxylic acids or else in the presence of a compound which contains a secondary amino group and a carbonyl group, the reaction giving good yields of the desired 3-substituted 3-formylacrylic ester when the glyoxylic ester is initially reacted with the alkanal under defined mild conditions to give a novel 3-substituted 2-hydroxy-3-formylpropionic ester of the formula I, and the latter is treated with a dehydrating agent, preferably with acetic anhydride, to give the desired 3-substituted 3-formylacrylic ester.

The reaction between glyoxylic ester and alkanal is thus, according to the invention, carried out in two stages. To prepare the novel 2-hydroxy-3-formylpropionic esters of the formula I, the reactants are slowly and simultaneously added, preferably in the form of a mixture, especially of an equimolar mixture of glyoxylic ester and alkanal, to the specific catalyst system, or else the alkanal is slowly added to a mixture of the catalyst system and the glyoxylic ester. It is possible in this way very easily to control the evolution of heat. The glyoxylic ester and alkanal combine in this first reaction step to give a novel 3-monosubstituted 2-hydroxy-3-formylpropionic ester of the formula I.

The measures used in the procedure according to the invention border on the measures employed in DE 36 17 409 for condensing glyoxal monoacetals with alkanals. Whereas the condensation therein is carried out very successfully in the presence of, particularly preferably, from 20 to 100 mol % catalyst based on starting material, under these conditions the condensation of methyl glyoxylate with propanal gives, with great effort, only a moderate yield of a colored product which is not stable on storage (see Example No. 4).

By contrast, in the presence of a very small amount of a catalyst composed of carboxylic acid and sec. amine, it is found, all the more surprisingly, that glyoxylic esters or hemiacetals thereof form with alkanals not the expected 3-formyl-3-alkylacrylic esters but the novel 2-hydroxy-3-formyl-3-alkylpropionic esters.

The present invention therefore also relates to a process for preparing the novel 3-substituted 2-hydroxy-3-formylpropionic esters of the formula I

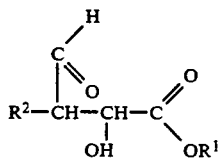

where
R$^1$ is alkyl of 1 to 4 carbon atoms, and
R$^2$ is straight-chain or branched alkyl of 1 to 10 carbon atoms, which comprises either an alkanal of the formula II

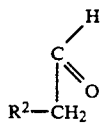

and an alkyl glyoxylate of the formula III

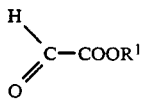

where R$^1$ and R$^2$ have the abovementioned meanings, being added simultaneously to a catalyst system composed of a salt of a secondary amine with a carboxylic acid or an approximately equimolar mixture of a secondary amine and a carboxylic acid, or a compound which contains a secondary amino group and a carboxyl group, in such a way that the temperature does not exceed 90° C., preferably 80° C., or else the alkanal of the formula II being added to a mixture of the catalyst system described above and the glyoxylic ester of the formula III in such a way that the temperature does not exceed 90° C., preferably 80° C., where the catalyst system is used in an amount of from 0.01 to 10 mol % preferably 0.1 to 8 mol %, especially 0.5 to 5 mol %.

Alkanals of the formula II which can be employed are propionaldehyde, butyraldehyde, valeraldehyde, isovaleraldehyde, isomeric hexanals, heptanals, octanals, nonanals, decanals, undecanals and dodecanals.

The process according to the invention is particularly important for reacting alkyl glyoxylates with alkanals of the formula II where R$^2$ is alkyl of 1 to 5 carbon atoms, especially for reacting with propionaldehyde.

The alkyl glyoxylates of the formula III can be prepared by oxydehydrogenation of the corresponding glycolic esters. The commercial products are in part obtained in oligomerized form, but can be monomerized by treatment with traces of acids. The process according to the invention is particularly important for reacting methyl glyoxylate.

Suitable catalysts for the first reaction step are salts or 1/1 mixtures of a secondary amine and a carboxylic acid. Suitable amines are aliphatic amines such as dimethylamine, diethylamine, dipropylamine, dibutylamine, methylethylamine, methylpropylamine, methylbutylamine, methylcyclohexylamine and substituted amines such as methylethanolamine and diethanolamine or cyclic amines such as pyrrolidine, piperidine or morpholine.

Examples of suitable carboxylic acids are acetic acid, propionic acid, butyric acid, valeric acids, hexanoic acids and 2-ethylhexanoic acid, and substituted carboxylic acids such as methoxyacetic acid or butoxy-acetic acid.

Particularly effective catalysts are those which combine the amine and acid functionalities in the same molecule, such as piperidine-2-carboxylic acid, pyrrolidine-2-carboxylic acid (proline) and, in particular, N-methylaminoacetic acid (sarcosine).

The catalysts are normally used in amounts of from 0.01–10 mol % based on the glyoxylic ester employed, preference being given to 0.1–8 mol % and, in particular, 0.5–5 mol %.

The reaction is generally carried out at from 20 to 90° C., preferably from 30 to 80° C.

To prepare the desired 3-substituted 3-formylacrylic esters of the formula IV

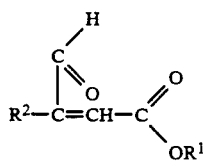

where R$^1$ and R$^2$ have the abovementioned meanings, it is possible to treat the 2-hydroxy-3-formylpropionic esters of the formula I according to the invention with a dehydrating agent.

Elimination of water from the 2-hydroxy-3-formylpropionic esters of the formula I can be carried out after isolation thereof but is done with particular advantage directly on the reaction mixture obtained according to the invention.

The elimination of water can be carried out by treating the 2-hydroxy-3-formyl-3-alkylpropionic esters according to the invention with catalytic amounts of an acid or, preferably, with acetic anhydride.

Although heating with acetic anhydride to eliminate water is recommended only for the more easily dehydratable 3-hydroxy carboxylic acid derivatives (cf. Houben-Weyl, Methoden der Organischen Chemie, Vol. 5/1b, p. 79, Georg Thieme Verlag Stuttgart, 1972), the dehydration of the 2-hydroxy-3-formyl-3-alkylpropionic esters to 3-formyl-3-alkylacrylic esters takes place in a surprisingly straightforward manner by heating with acetic anhydride.

The procedure is to add from 1 to 5 moles of acetic anhydride and, where appropriate, small amounts of a catalyst such as sodium acetate or 4-dimethylaminopyridine per mole of reaction mixture obtained according to the invention, and then to reflux it for from 1 to 12, preferably 2 to 6, hours, remove the acetic acid which is formed by distillation, and fractionally distil the residue under reduced pressure.

The overall process which results and which can be used to prepare the highly desirable precursors for vitamin A acid, the alkyl 3-formylcrotonates of the formula IVa

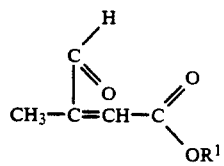

(IVa)

where
R¹ is alkyl of 1 to 4 carbon atoms, in yields of up to 80% or more, comprises A. either adding propionaldehyde and an alkyl glyoxylate of the formula III

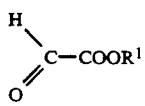

(III)

where R¹ has the abovementioned meaning, simultaneously to a catalyst system composed of a salt of a secondary amine with a carboxylic acid or an approximately equimolar mixture of a secondary amine and a carboxylic acid, or a compound which contains an equal number of secondary amino groups and carboxyl groups, in such a way that the temperature does not exceed 90° C., preferably 80° C., or adding the alkanal to a mixture of the catalyst system and the glyoxylic ester in such a way that the temperature does not exceed 90° C., preferably 80° C., and B. treating the resulting reaction mixture with acetic anhydride.

The process according to the invention can be used to prepare in a very advantageous manner the desirable ethyl 3-formylcrotonate and the 3-substituted 3-formyl acrylic esters which are of great interest as intermediates, in yields of up to 80% or more. In addition, novel intermediates of interest are made available.

EXAMPLE 1

Comparative Example based on DE 1 008 729, Example 1

3.2 g (0.025 mol) of di-n-butylamine were added to a boiling, at 70° C., mixture of 120 g (1 mol) of methyl 2-methoxy-2-hydroxyacetate and 58 g (1 mol) of propionaldehyde. An exothermic reaction started immediately and the temperature rose to 100° C., when part of the reaction mixture boiled out of the flask. The temperature slowly fell to 90° C. and was maintained at this for 30 min. Fractional distillation of the reaction mixture yielded 38.9 g of methyl 3-formylcrotonate of boiling point (b.p.) 56°–68° C./10 mbar, corresponding to a yield of 30.4% of theory. The trans/cis ratio was determined by gas chromatography to be 83/17.

EXAMPLE 2

Comparative Example based on DE 1 008 729, Example 1

3 g (0.025 mol) of di-n-butylamine were added at 20° C. to a stirred mixture of 88 g (1 mol) of methyl glyoxylate and 58 g (1 mol) of propionaldehyde. An exothermic reaction started immediately and the temperature of the reaction mixture rose to about 60° C. and it boiled vigorously. After about 1 min the temperature again rose rapidly and remained at about 130° C. for about 5 min. It then fell to about 80° C. over the course of 20 min; after standing overnight it had fallen to room temperature. Distillation of the reaction mixture yielded 75 g of product fractions of b.p. 60°–73° C./30 mbar, which contained a total of 68 g of methyl 3-formylcrotonate, corresponding to a yield of 53% of theory. The trans/cis ratio was determined by gas chromatography to be 84/16.

EXAMPLE 3

Comparative Example based on DE 1 008 729, Example 1

3 g (0.025 mol) of di-n-butylamine were added at 20° C. to a stirred mixture of 120 g (1 mol) of methyl 2-methoxy-2-hydroxyacetate and 58 g (1 mol) of propionaldehyde. An exothermic reaction started immediately and the temperature of the reaction mixture rose to about 90° C., and it boiled vigorously. After about 10 min the temperature started to fall again and reached room temperature after about 1.5 h. Distillation of the reaction mixture yielded 66.4 g of methyl 3-formylcrotonate of b.p. 45°–58° C./8–9 mbar, corresponding to a yield of 52%. The trans/cis ratio was determined by gas chromatography to be 91/9.

EXAMPLE 4

Comparative Example based on DE 36 17 409

A mixture of 60 g (i mol) of acetic acid and 112.5 g (1 mol) of 40% by weight aqueous dimethylamine solution was heated to 50° C. and then cooled in ice-water and, while stirring, a mixture of 88 g (1 mol) of methyl glyoxylate and 116 g (2 mol) of propionaldehyde was added within 10 min. Despite cooling in ice, the temperature rose to about 70° C.

After the dropwise addition was complete the mixture was immediately cooled with ice-water, 200 ml of ethyl acetate were added, the organic phase was separated off, and the aqueous phase was extracted five more times with ethyl acetate. The combined organic phases were distilled. Two distillations resulted in 50 g of methyl 3-formylcrotonate of b.p. 54° C./1 mbar, corresponding to a yield of 39% of theory, based on glyoxylic ester. The product was red in color and decomposed on storage.

EXAMPLE 5

18 g (0.2 mol) of sarcosine were suspended by stirring in 500 ml of cyclohexane in a flask and, starting at 20° C., a mixture of 1809 g (20.6 mol) of methyl glyoxylate and 1194 g (20.6 mol) of propionaldehyde was added within 90 min. During the dropwise addition the temperature rose slowly to the boiling point (75° C.). After the addition was complete, initially a small amount of water was removed as azeotrope, and then the mixture was distilled until the bottom temperature was 100° C. to remove cyclohexane. Then 2220 g (21.8 mol) of acetic anhydride were added to the residue, and the reaction mixture was distilled to a bottom temperature of 150° C. to remove acetic acid. Fractional distillation of the bottom product yielded 1822 g (14.2 mol) of methyl 3-formylcrotonate, corresponding to a yield of 69% of theory, with a trans/cis isomer ratio of 93/7.

EXAMPLE 6

A mixture of 264 g (3 mol) of methyl glyoxylate and 348 g (6 mol) of propionaldehyde were added to a stirred and cooled mixture of 18 g (0. 3 mol) of acetic acid and 34 g (0.3 mol) of 40% by weight aqueous dimethylamine solution in such a way that the temperature did not rise above 70° C. After the addition was complete, the mixture was cooled and extracted several times with ethyl acetate. Catalyst residues were removed by treating the extracts with a mixed bed ion exchanger and then distilling them. The distillate boiling in the range 40°-75° C./1 mbar weighed 236 g and, according to the gas chromatogram, contained 90% methyl 2-hydroxy-3-methylbutanoate, and the subsequent fraction boiling in the range 75°-100° C. weighed 64 g and contained 53% methyl 2-hydroxy-3-methylbutanoate. The total yield was thus 246.3 g of hydroxy ester, corresponding to 56% of theory.

EXAMPLE 7

A mixture of 57 g (0.5 mol) of n-heptanal and 44 g (0.5 mol) of methyl glyoxylate was added dropwise to a mixture of 1.85 g (0.025 mol) of propionic acid and 3.22 g (0.025 mol) of di-n-butylamine in such a way that the temperature did not exceed 80° C. After the addition was complete the mixture was stirred at 80° C. for 30 min, then 102 g (1 mol) of acetic anhydride were added and the mixture was heated to boiling. Acetic acid slowly distilled out, 51 g being obtained in 2 hours. Fractional distillation of the bottom product yielded 59 g of methyl 3-formyl-3-pentylacrylate with a boiling point of 82°-85° C./1 mbar, corresponding to a yield of 64% of theory. The trans/cis isomer ratio was 78/22.

EXAMPLE 8

688 g (11.9 mol) of propionaldehyde were added within 45 min to a mixture of 968 g (11 mol) of methyl glyoxylate, 352 g (11 mol) of methanol and 9.6 g (0.11 mol) of sarcosine at 50° C. After the addition was complete, the mixture was stirred at 80° C. for 1 h and then 2805 g (27.5 mol) of acetic anhydride were added. Distillation was carried out under atmospheric pressure with a column until the top temperature was 105° C., to remove some of the methyl acetate/acetic acid, and then up to 125° C. to remove a mixture of methyl acetate, acetic acid, acetic anhydride and methyl 3-formylcrotonate. Distillation was then continued under 250 mbar up to 105° C. and then under 30 mbar until the top temperature was 90° C. The combined distillates were redistilled to give 1184 g (9.3 mol) of methyl 3-formylcrotonate, corresponding to a yield of 84% of theory.

EXAMPLE 9

174 g (3 mol) of propionaldehyde were added within 1 h to a mixture of 264 g (3 mol) of methyl glyoxylate, 96 g of methanol and 2.7 g (0.03 mol) of sarcosine at 80° C. After the addition was complete the reaction mixture was stirred at 80° C. for 1 h and then distilled under a pressure of 1 mbar in a thin-film evaporator. 417 g of distillate which contained 50.8% methyl 2-hydroxy-3-formylbutanoate and 16.4% methyl formylcrotonate were obtained.

We claim:
1. A process for preparing a 3-substituted 2-hydroxy-3-formylpropionic ester of the formula I:

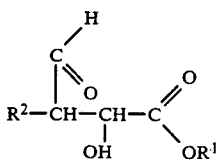
(I)

where
R¹ is alkyl of 1 to 4 carbon atoms, and
R² is straight-chain or branched alkyl of 1 to 10 carbon atoms,
which comprises an alkanal of the formula II

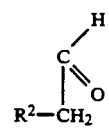
(II)

and an alkyl glyoxylate of the formula III

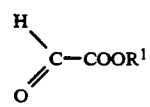
(III)

where R¹ and R² have the above-mentioned meanings, being added simultaneously to a catalyst system composed of a salt of a secondary amine with a carboxylic acid or an approximately equimolar mixture of a secondary amine and a carboxylic acid, or a compound which contains a secondary amino group and a carboxyl group, in such a way that the temperature does not exceed 90° C., or else the alkanal of the formula II being added slowly to a mixture of the catalyst system described above and the glyoxylic ester in such a way that the temperature does not exceed 90° C., where the catalyst system is used in an amount of from 0.01 to 10 mol %, based on the glyoxylic ester.

2. A process as claimed in claim 1, wherein propionaldehyde is used as alkanal of the formula II.

3. A process for preparing a 3-substituted 3-formylacrylic ester of the formula IV

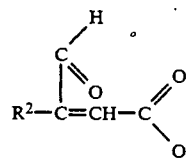
(IV)

where R¹ and R² have the meanings stated in claim 1, which comprises a 2-hydroxy-3-formylpropionic ester of the formula I obtained by the process claimed in claim 1 being treated with a dehydrating agent.

4. A process for preparing a 3-substituted 3-formylacrylic ester of the formula IV

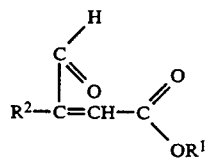
(IV)

where R¹ and R² have the meanings stated in claim 1, which comprises the reaction mixture which is obtained by the process claimed in claim 1, and contains a 2-hydroxy-3-formylpropionic ester of the formula I being treated with acetic anhydride.

5. A process as claimed in claim 1, which comprises either adding propionaldehyde and an alkyl glyoxylate of the formula III

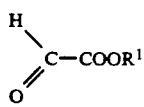

where $R^1$ has the abovementioned meaning, simultaneously to a catalyst system composed of a salt of a secondary amine with a carboxylic acid or an approximately equimolar mixture of a secondary amine and a carboxylic acid, or a compound which contains a secondary amino group and a carboxyl group, in such a way that the temperature does not exceed 90° C., or adding the alkanal of the formula II to a mixture of the catalyst system described above and the glyoxylic ester of the formula III in such a way that the temperature does not exceed 90° C., and converting the alkyl 3-formyl-2-hydroxybutanoate of the formula Ia

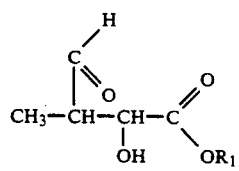

where $R^1$ is alkyl of 1 to 4 carbon atoms, by treatment with acetic anhydride into the corresponding alkyl 3-formylcrotonate of the formula IVa

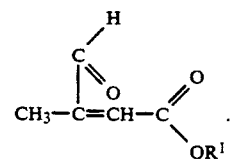

* * * * *